United States Patent [19]

Sawyer

[11] 4,238,480

[45] Dec. 9, 1980

[54] METHOD FOR PREPARING AN IMPROVED HEMOSTATIC AGENT AND METHOD OF EMPLOYING THE SAME

[76] Inventor: Philip N. Sawyer, 7600 Ridge Blvd., Brooklyn, N.Y. 11209

[21] Appl. No.: 907,899

[22] Filed: May 19, 1978

[51] Int. Cl.² ............... A23J 1/10; A61L 17/00
[52] U.S. Cl. ................... 424/177; 128/325; 128/334 R; 128/DIG. 8; 260/123.7; 435/177; 260/117
[58] Field of Search ............... 260/117, 123.7; 424/177

[56] References Cited

U.S. PATENT DOCUMENTS

| | | | |
|---|---|---|---|
| 3,682,825 | 8/1972 | Tamai et al. | 260/117 |
| 3,697,437 | 10/1972 | Fogle et al. | 260/117 |
| 3,742,955 | 7/1973 | Battista et al. | 128/334 R |
| 4,043,952 | 8/1977 | Ganslaw et al. | 260/117 |

FOREIGN PATENT DOCUMENTS 256785  1/1963  Australia ............... 260/123.7

OTHER PUBLICATIONS

Peacock et al., Ann. Surg., vol. 161 (1965), pp. 238–247.

*Primary Examiner*—Walter C. Danison
*Attorney, Agent, or Firm*—Posnack, Roberts, Cohen & Spiecens

[57] ABSTRACT

An improved hemostatic agent is made by treating collagen or collagen-like substance to render the surface charge thereof effectively more positive. The thusly modified substance is employed to control or terminate bleeding.

26 Claims, 6 Drawing Figures

METHOD FOR PREPARING AN IMPROVED HEMOSTATIC AGENT AND METHOD OF EMPLOYING THE SAME

FIELD OF THE INVENTION

This invention relates to hemostatic agents and to method of preparing and using the same.

BACKGROUND

In various prior patents, there have been discussions of the modification of the surface charge of vascular systems or substances to be used in association therewith. Generally, it has been suggested that such systems be dealt with to make the surface charge thereof more negative to avoid thrombosis and the like.

A variety of hemostatic agents are known such as Gelfoam TM manufactured by Up-John and disclosed in U.S. Pat. No. 2,465,357; Avitene TM manufactured by Acecon and disclosed in U.S. Pat. No. 3,742,955 and Surgicell TM manufactured by Johnson and Johnson and disclosed in U.S. Pat. No. 3,364,200.

Battista et al in Patent 3,742,955 report that collagen in various treated or prepared forms is useful in surgery and for the treatment of wounds, and that E. Peacock, Jr. et al Ann. Surg. 161,238-47, February, 1965 teaches that collagen has hemostatic properties when used as a wound dressing. Battista et al further report that it has been found that fibrous collagen and fibrous products derive from collagen when properly prepared and when wet with blood will not only demonstrate hemostasis, but also demonstrates an unexpected adhesiveness to severed biological surfaces in warm blooded animals. They also provide a method of preparing finely divided fibrous collagen and fibrous products derived from collagen which are useful hemostatic agents and have unique adhesive properties in contact with a severed biological surface in a warm blooded animal when wet with blood.

Ashton et al report in U.S. Pat. No. 3,364,200 that surgical hemostats consisting of conventional gauze pads or similar articles impregnated with a hemostatic material such as ferric chloride, thrombin or the like, have been used for many years to arrest bleeding. However, the prior art hemostats are criticized in that they cannot be left in situ in a closed wound since foreign body tissue reaction would result, this being a serious disadvantage inasmuch as removal of the hemostat from the bleeding sight would disrupt any blood clot which has formed to cause renewed bleeding. Ashton et al observed, therefore, that a vital need exists for a hemostatic material which could be left in place in a closed wound without causing serious local tissue reaction. It is also reported that improvement was provided when it was discovered that oxidized cellulose not only had hemostatic properties but also was absorbable in animal tissue. Ashton et al provide oxidized cellulose absorbable hemostats having improved stability against deterioration on storage. The oxidized cellulose is derived from wood pulp, cotton, cotton linters, ramie, jute, paper and similar materials and regenerated cellulose or rayon produced by either the viscose or Bemberg processes.

Correll's U.S. Pat. No. 2,465,357 relates to a liquid-permeable, water-insoluble, gelatin sponge having general physical characteristics of a sponge but being absorbable by animal bodies. The sponge is a porous substance which according to the disclosure, should be reasonably soft when wet and have many fine interstices in order to hold a quantity of a therapeutic agent and to discharge the same slowly or act as an efficient absorbative material for free flowing fluids in a wound area such as blood and exudates. Correll discloses preparing an aqueous solution containing gelatin and adding a small amount of formalin and thereafter beating the material for an extended period of time to produce a firm foam of substantially greater than the volume of the original solution.

The above inventions are of interest in the field of hemostasis, however, none of the patents listed above deal with the controlling of the surface electronic or electrostatic charge of the materials involved and consequently did not go to the basis of the hemostasis problem as in accordance with the present invention.

In addition to the above, a discussion of collagen sponge appears in Collagen Sponge: Theory and Practice of Medical Applications, J. Biomedical Materials Research (John Wiley & Sons, New York) Vol. 11 No. 5, September, 1977. In this article, applications of collagen as a biodegradable material is reviewed inclusive of rate of resorption and antigenicity.

SUMMARY OF THE INVENTION

It is an object of the invention to provide an improved hemostatic agent.

Another object of the invention is to provide an improved method for preparing hemostatic agents.

Yet another object of the invention is to provide an improved method of utilizing hemostatic agents.

To achieve the above and other objects of the invention, there is provided a method comprising modifying one of the group consisting of a collagen substance or a collagen-like substance to render the surface charge thereof effectively more positive, and applying the thusly modified substance to control bleeding.

According to one specific embodiment of the invention, the substance may be modified by non-convalent modification. Furthermore, this substance is lyophilized.

According to another embodiment of the invention, the substance may be modified by covalent modification. This substance is also lyophilized in a preferred modification thereof.

According to the invention, there is provided a hemostatic agent prepared as indicated above. The collagen or collagen-like substance which is employed may preferably be gelatin which is treated with hydrochloric acid.

According to a feature of the invention, the gelatin may be treated with ethylenediamine.

The above and other objects, features and advantages of the invention will be found in the detailed description which follows hereinafter.

DETAILED DESCRIPTION

The purpose of this invention is to provide a chemically modified collagen or collagen-like substance as a hemostatic agent which is competitive with commercially available products and which is superior thereto in certain respects.

The substance of the invention is a collagen or collagen-like compound, modified with positive moieties, which can be used clinically to control bleeding especially in non-suturable areas. It is meant to be an adjunct to and not a replacement of conventional surgical procedures.

Many factors contribute to the clotting mechanism of hemostatic agents. Some of these are: (1) surface chemistry (including biochemical interactions), (2) electrical or electrostatic charge characteristics, and (3) micro structure. In the preliminary stages of synthesizing and evaluating hemostatic agents, an attempt has been made to recognize the importance of each of the above criteria.

The various forms of the hemostatic agent provided by the invention are modifications of collagen or a collagen-like compound. Collagen itself demonstrates hemostatic properties. The modifications which have been attempted seek to augment these phenomena both by manipulating the surface charge and micro structure.

The modification of a compound charge density can be achieved by two distinct methods; (1) non-covalent modification of dissolved bone gelatin (Baker U.S.P.) using positive groups, such as provided by HCl, (2) covalent attachment of a variety of ligands to the peptide chain of gelatin.

The preparation of multiple forms of a positively charged hemostatic agent are synthesized as shown below based by way of example on the following initial preparation of a collagen or collagen-like substance or compound:

By way of example, one liter of 1% (or 10 grams for 1 liter) stock solution of gelatin (Baker U.S.P. crude) is dissolved in distilled and deionized water at room temperature with constant stirring. From this stock solution, 200 ml. aliquots are withdrawn and used in the various techniques given below.

A. Non-Covalent Modification

The 200 ml. aliquot of protein solution is adjusted to desired pH (e.g., pH=2.5) with a 1% gel (low density) HCl (LDHCl). For pH=3.0, a 5% gel (high density) HCl (HDHCl) is used. To the solution is added 1 N HCl, which is diluted from a concentrated HCl (Fisher reagent grade). This is done with constant stirring to insure hemogenicity and to minimize any denaturation.

The gelatin-HCl solution is then stirred for two hours at room temperature, filtered through a Whatman No. 4 filter into a 600 ml Virtus flask. The flask is then immersed in a dry-ice acetone bath ($-40°$ C.) and, with constant swirling of the flask, the protein solution inside becomes shell frozen. This material is then placed on a Virtus lyophilizer (Research Equipment, N.Y.) and dried until the solution has a foam-like character. The material is then removed from the Virtus flask and placed into desiccator glass or plastic bottles. Alternatively, shelf-freezing techniques are employed.

A second modification is the addition of $CaCl_2$ $2H_2O$ (Fisher reagent grade) to the purified gelatin in final $Ca^{++}$ concentrations of 0.001 M, 0.01 M, 0.10 M or 0.25 M (Table 1).

B. Covalent Modification

The covalent attachment is obtained utilizing the structure of collagen or gelatin as a support media (considering it to be, for example, similar to a Sephrose ® matrix with its free carboxylic acid end groups) and binding the ligand to this matrix through a peptide bond created between the end —COOH groups of the gelatin and the free amino groups of the various ligands.

This peptide bond formation occurs easily at pH 4.75 with the use of the condensing agent 1 ethyl-3 (3 dimethylaminopropyl) carbodiimide—HCl (E.D.C. purchased from Sigma Corp.)

This bond formation is explained since the bone gelatin used is assumed to be similar in amino acid composition to bovine bone collagen. Bovine bone collagen possesses 44 aspartic acid groups, and 77 glutamic acid groups or, in other words, 121 COOH per 1000 residues. Based on the above analysis, it can be assumed that the gelatin in this experiment contains 100/1000 free carboxylic acid groups. Thus, 100 mg/1 gm of gelatin should be modified if the modifying ligand is in large excess. All other modifications were carried out analogously.

Example

To a 200 ml aliquot of protein solution was added enough ligand (1 molar) to be in 5X excess of the possible binding sites. The solution was adjusted to a pH of 4.75 with the use of an appropriate acid (HCl) or base (NaOH). To this stirring solution was added 5 gms. solid EDC (minimum carbodiimide required to make a final concentration of 0.1 M) The solution was then stirred for 2 hours. The reaction was followed by measurement with a Leeds-Northrop pH meter. There was a change in pH (i.e. to pH=3) which was compensated for by the addition of base. The sample was then stirred for 24 hours, in order to insure complete reaction of all possible binding sites.

The protein was then dialysed with the use of running water for 6 hours and again against 4 liters of distilled and deionized water for 2 hours repeated four times. This was to assure removal of all unreacted ligand and condensing agent. The material was then filtered and handled identically to the non-covalently modified material (shell frozen and lyophilized).

| CODE NO. | GELATIN | EXAMPLES LIGAND | EDC | BINDING |
|---|---|---|---|---|
| 1. | 1% | — | — | — |
| 2. | 1% | HCl | — | non covalent |
| 3. | 1% | $NH_4Cl$ | 5gms | covalent |
| 4. | 1% | — | 5gms | Internal |
| 5. | 1% | Ethylenediamine | 5gms | Covalent[1] |
| 6. | 1% | $AlCl_3$ | — | Covalent |
| 8. | 5%[2] | — | — | Covalent[1] |
| 9. | 5%[2] | HCl | — | non-covalent |
| 10. | 1% | $AlCl_3$ + Urea | 5gms | covalent |

[1] The covalent nature of this binding has yet to be established quantitatively.
[2] The change to 5% (high density) was indicated when evaluating the 1% foams as these examples were extremely hydroscopic and dissolved quickly in profuse bleeding.

In an effort to quantify what chemical modifications of the collagen were actually occurring, the following analytical procedures were used:
1. polyacrylamide disc electrophoresis (P.A.G.E.)
2. binding studies
3. circular dichromism studies P.A.G.E. is a widely used technique for visualizing purity, mass and charge of a protein. Proteins migrate through a medium on the basis of charge/mass (e/m)

ratios. Since the migration of protein is due to this ratio, it is possible to use this technique to evaluate either criteria.

More conventionally, the criterion evaluated by this technique is mass (S.D.S. denaturing gel electrophoresis) though, with some slight modifications, the banding pattern of a protein could be used to discriminate between identical mass proteins with modified charge characteristics. The technique can also be used to detect the quantity of any charge alteration due to modifying collagen, without resorting to the more difficult, expensive, through conventional isoelectric focusing.

As to binding studies, it is apparent that binding studies must be used to determine the type and quantity of modifications made. The covalent modification used in this procedure creates in essence pseudo lysine residues. Any technique which can differentiate free $NH_2$ groups on an intact protein can be used to determine the amount of binding by comparing the number of $NH_2$ groups both pre and post treatment. Such techniques include ninhydrin assay, and/or fluorescamine assay (Purcell et al).

Finally, the conformation of a protein determines to some extent its chemical properties. It is therefore helpful to monitor any alteration of chemical conformation caused by a modification by means of circular dichromism studies both before and after treatment. Ultimately, correlation should be established between alterations of conformation with clotting properties.

To evaluate the materials synthesized, there have been utilized acute in vivo animal experiments (dog) and in vitro TRT (thrombin recalcification time) analysis.

The evaluation of the hemostatic agents of the invention and comparison thereof consisted of: (1) Subcutaneous implantation of a variety of agents in a given animal for a period ranging from one day, 2 days, 7 days and 2 weeks, (2) bleeding time and semi-quantitative analysis of the weight of blood loss in two separate anatomical locations (skin and spleen). From these tests, there was obtained information on (1) relative clottability (efficacy) of each of the agents, (2) information on the physical structural integrity of these materials both before and after contact with blood, (3) gross indications of toxicity and histology, (4) different types of fibrin formed when exposed to blood from different areas which is dependent on both the properties of the agent and the properties of the blood involved, (5) handling characteristics of each agent under operating room conditions, and (6) clinician's subjective opinions of each agent as it relates to handling, clottability and interaction with surrounding tissue.

Implantation studies were accomplished by creating a pocket in the muscularis of the chest (dog) and placing each agent in individual pockets, and suturing them closed with silk. The samples were excised prior to sacrifice, fixed in formalin-glutaraldehyde and marked for histological and microscopic examination. The samples obtained are as follows:

| DATE | No. of DOGS | ORDER | COMMENTS |
| --- | --- | --- | --- |
| 2/1/77 | D6:45 | No. 0,I,III,II,1,2, 3,5,4 | No. 5 = wet and slippin No. 4 = crystalline |
| 2/1/77 | D6:53 | No. 6,I,III,II,1,2, 3,5,4 | No. 3 = was wet and crystalline No. 4 = caused abscess |

-continued

| DATE | No. of DOGS | ORDER | COMMENTS |
| --- | --- | --- | --- |
| 2/1/77 | 45:131 | No. 4,0,I,III,II,1,2, 3,5,10,9 | No. 6 = turned blood brown No. 10 on right side |
| 2/23/78 | C6:18 | No. 8,11,12,13,14 | |

Key:
- 0 = control no agent
- I = Gelfoam
- II = Surgicell
- III = Avitene
- 1 = gelatin foam 1%
- 2 = gelatin foam 1% = HCl
- 3 = gelatin foam 1% + $NH_4Cl$ + EDC
- 4 = gelatin foam 1% + EDC
- 5 = gelatin foam 1% + EDA + EDC
- 6 = gelatin foam 1% + $AlCl_3$
- *7 = gelatin foam 1% (2 week implantation in neck)
- 8 = gelatin foam 5%
- 9 = gelatin foam 5% + HCl
- 10 = gelatin foam 1% + $AlCl_3$ + Urea + EDC
- 11 = gelatin foam 5% + 0.001M $CaCl_2$
- 12 = gelatin foam 5% + .010M $CaCl_2$
- 13 = gelatin foam 5% + .10M $CaCl_2$
- 14 = gelatin foam 5% + .25M $CaCl_2$

*N.B. No. 7 and No. 1 are identical compounds.

In addition, photographic evaluations were made of all sites at the 1, 2, and 7 day interval.

The results of these implantation studies and structural investigation are summarized in Tables 1 and 2.

Skin Incision Healing Time

A 3 cm incision was made into the left or right torso of the dog, which penetrated the muscularis. Then the hemostatic agent was added and the incision was allowed to clot. There was no pressure placed on any of the agents. The time to clot was obtained via stop watch.

In one set of experiments, under each incision was placed a pre-weighed 4×4 bandage or sponge and the blood was collected and weighed. The weight of the blood was obtained by subtracting the weight of the clean dry 4×4 sponge from the weight of the blood soaked 4×4 bandage or sponge. The results are tabulated in Table 2.

Organ Bleeding Time

In order to obtain information on the relative hemostatic ability of each of the agents on a non-suturable organ such as the spleen or liver, incisions were made on the spleen and the bleeding times were obtained. The procedure was essentially analogous to the forementioned skin test. A 3 cm incision was made in the lateral aspect of the spleen, the hemostatic agents were placed on the injury and the bleeding time and weight of blood were obtained. There was some difficulty noted in evaluating this data as, with different degrees of injury (i.e. cut arteries, etc.), there were differential bleeding rates. This is noted when necessary on the results. The spleen was then excised, fixed and marked for histologic evaluation.

In Vitro Analysis

An in vitro analysis consisting of standard TRT (thrombin recalcification time) substituting dissolved hemostatic agents at the same concentration for normal saline was made.

RESULTS

The results indicate that a number of varieties of the hemostatic agent of the invention are viable alternatives to those hemostatic agents commercially available (Avitene, Surgicell and Gelfoam) in both hemostatic ability and histological evaluation. These are H.D. HCl (high density 5% HCl treated), L.D. HCl (low density 1% HCl treated), and LDO (low density 1% gelatin). Furthermore, the investigators and clinicians involved in this preliminary study listed the order of preference of hemostatic agents as H.D. HCl, L.D. HCl, Avitene, L.D.O., Surgicell and Gelfoam.

The results indicated above are tabulated in the following Tables 1 and 2.

TABLE NO. 1

| Product code # | Modification | Structure | Ultra physical structure upon exposure to blood | Anatomical test location Sp(spleen) Sk (skin) | Blood loss | Adhesion to wound | Handling characteristics | Tissue healing | Clot formation | Histologic data 1 day | 2 day | 7 days | 2 wks |
|---|---|---|---|---|---|---|---|---|---|---|---|---|---|
| I | Gelfoam | 3 | 3 | Sp-Sk | 2 | 3 | 3 | 2 | 3 | 2 | 2 | 2 | |
| II | Surgicell | 4 | 4 | Sp-Sk | 2 | 3 | 4 | 2 | 3 | 1 | 1 | 2 | |
| III | Avitene | 1 | 2 | Sp-Sk | 3 | 2 | 1 | 2 | 2 | 1 | 2 | 2 | |
| 1 | 1% FG | 2 | 1 | Sp-Sk | 2 | 1 | 1 | 4 | 2 | 2 | 4 | 4 | 4 |
| 2 | 1% FG + HCl | 2 | 3 | Sp-Sk | 1 | 2 | 2 | 2 | 3 | 1 | 2 | 3 | |
| 3 | 1% FG + NH4Cl + EDC | 3 | 2 | Sp-Sk | 2 | 3 | 3 | 2 | 3 | 1 | 2 | 2 | |
| 4 | 1% FG + EDC | 2 | 2 | Sp-Sk | 3 | 2 | 3 | 2 | 3 | 2 | 2 | 3 | |
| 5 | 1% FG + EDA + EDC | 2 | 3 | Sp-Sk | 2 | 3 | 3 | 2 | 2 | 2 | 2 | 2 | |
| 6 | 1% FG + AlCl3 | 3 | 2 | Sp-Sk | 3 | 2 | 3 | 1 | 1 | 3 | 2 | 3 | |
| 8 | 5% FG | 3 | 4 | Sp-Sk | 1 | 4 | 3 | 4 | 3 | 2 | 3 | 4 | 4 |
| 9 | 5% FG + HCl | 3 | 4 | Sp-Sk | 1 | 4 | 4 | 3 | 3 | 2 | 2 | 3 | |
| 10 | 1% FG + AlCl3+Urea + EDC | 3 | 4 | Sk | 3 | 2 | 4 | 1 | 1 | — | — | — | 3 |
| 11 | 5% Gelatin foam + 0.001 M caCl2 | 4 | 4 | Sp-Sk | 1 | 4 | 4 | 4 | 4 | | | | 4 |
| 12 | 5% Gelatin foam + 0.1 M CaCl2 | 4 | 4 | Sp-Sk | 1 | 4 | 4 | 4 | 4 | | | | 3 |
| 13 | 5% Gelatin foam + 0.1 M caCl2 | 2 | 3 | Sp-Sk | 2 | 4 | 3 | 2 | 3 | | | | 2 |
| 14 | 5% Gelatin foam + 0.25 M caCl2 | 2 | 3 | Sp-Sk | 2 | 3 | 2 | 1 | 3 | | | | 1 |

FG = Foamed Gelatin
0 = None/None
1 = Poor/Minimal
2 = Good/Medium
3 = Very Good/Severe
4 = Excellent/Maximal

TABLE #2

BLEEDING TIME AND BLOOD LOSS IN SKIN AND SPLEEN INCISIONS

| ME | *Percent Change in Bleeding Time vs Control | *Percent Change In Weight of Total Bood Loss vs Control (gm.) | **Percent Change Bleeding Time vs Control | **Percent Change in Total Blood loss vs Control |
|---|---|---|---|---|
| CONTROL | 0 | 0 | 0 | 0 |
| Gelfoam | −24.8 | −73.0 | −65.9 | −70.0 |
| Surgicell | −26.0 | −78.8 | −78/5 | −68.7 |
| Avitene | −21.7 | +15.3 | −79.5 | −48.7 |
| Gelatin Foam 1% | −42.6 | −80.3 | −87.7 | −62.5 |
| Gelatin Foam 1% + HCl | −61.5 | −86.5 | −85.7 | −67.5 |
| Gelatin Foam 1% + NH4Cl + EDC | +01.0 | −85.3 | −78.2 | −68.0 |
| Gelatin Foam 1% + EDC | −03.0 | −82.3 | −61.9 | −64.0 |
| Gelatin Foam 1% + EDA + EDC | −16.6 | −78.0 | −72.1 | −60.7 |
| Gelatin Foam 1% + AlCl3 | +73.0 | +93.8 | −42.1 | −35.5 |
| Gelatin Foam 5% | −39.1 | −75.0 | −90.4 | −65.5 |
| Gelatin Foam 5% + HCl | −56.4 | −81.0 | −91.1 | −69.5 |
| Gelatin Foam 1% + AlCl3 + Urea + EDC | +98.7 | +56.9 | — | — |

TABLE #2-continued

BLEEDING TIME AND BLOOD LOSS IN SKIN AND SPLEEN INCISIONS

| ME | *Percent Change in Bleeding Time vs Control | *Percent Change In Weight of Total Bood Loss vs Control (gm.) | **Percent Change Bleeding Time vs Control | **Percent Change in Total Blood loss vs Control |
| --- | --- | --- | --- | --- |
| Gelatin Foam 5% + 0.001M CaCl$_2$ | −50.0 | −88.5 | −91.1 | −90.7 |
| Gelatin Foam 5% + .010M CaCl$_2$ | −56.2 | −94.6 | −93.8 | −12.5 |
| Gelatin Foam 5% + .10M CaCl$_2$ | −57.5 | −72.3 | −93.8 | −0.4 |
| Gelatin Foam 5% + .25M CaCl$_2$ | −56.2 | −92.1 | −94.5 | −0.1 |

*SKIN
**SPLEEN
− = decrease
+ = increase

Figure 1:
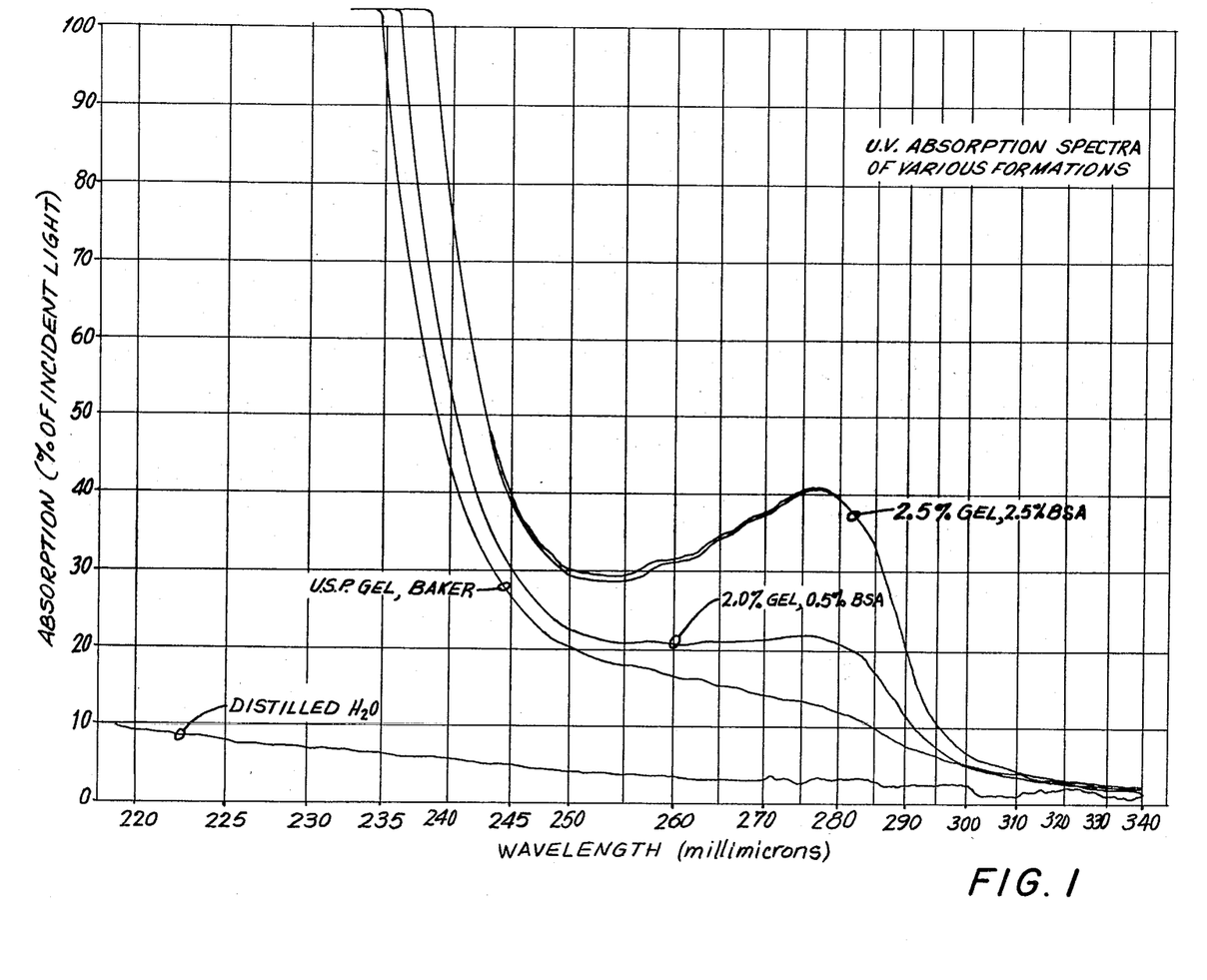
FIGS. 1–3 are charts showing the ultraviolet absorption spectra of various embodiments of the invention.
Figure 2:
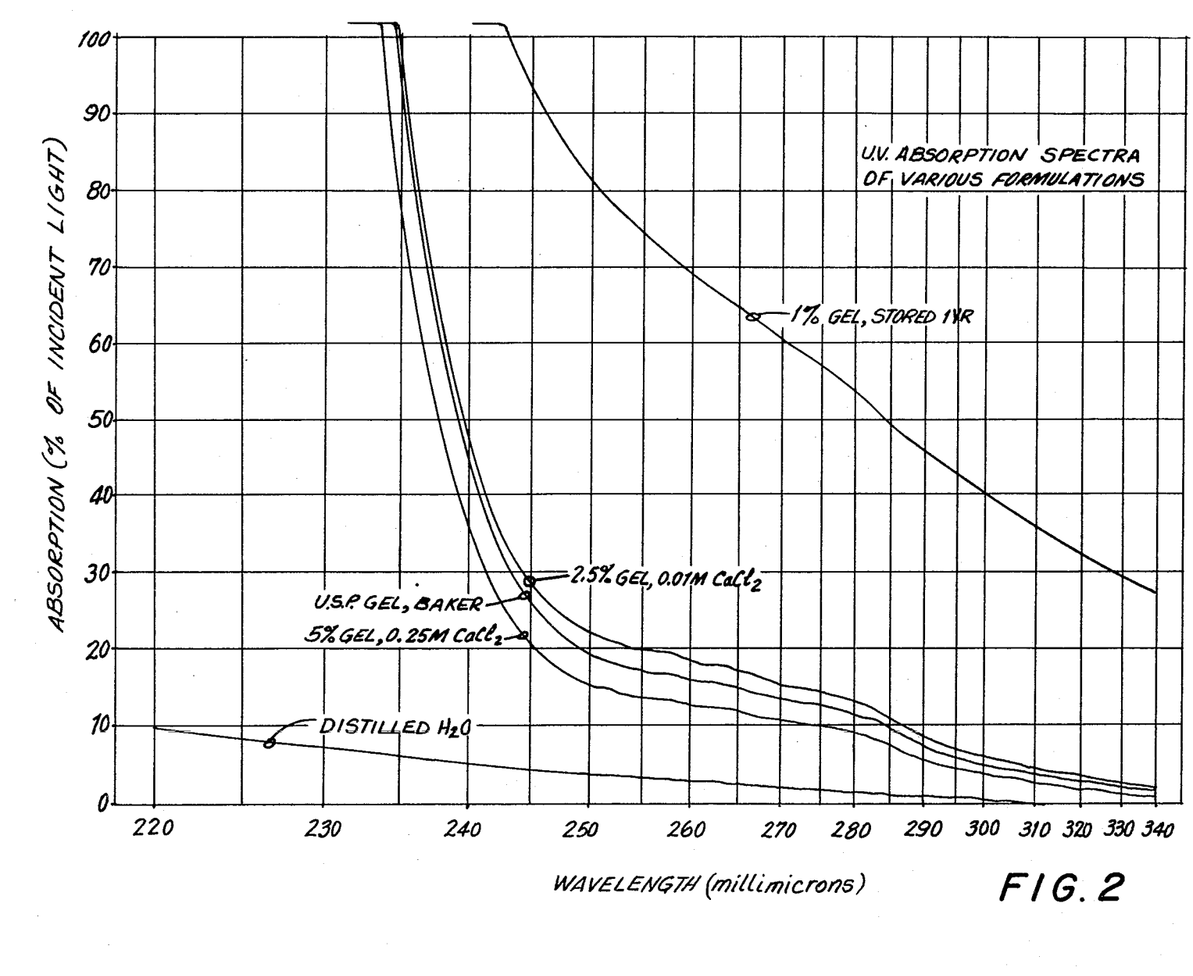
Figure 3:
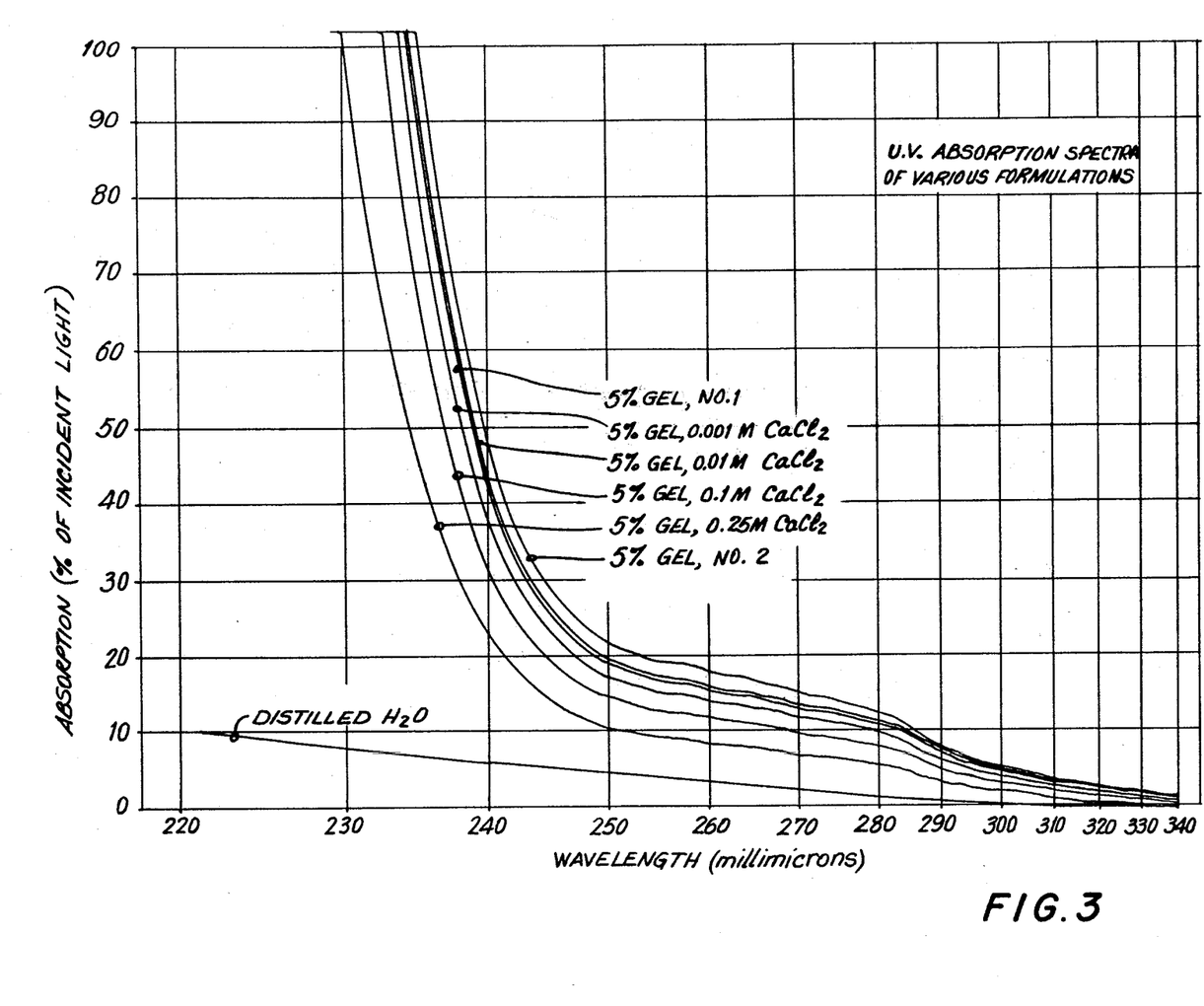

FIGS. 1-3 show U.V. absorption spectra of various formulations according to the invention. The basic compound alone or with CaCl$_2$ added does not absorb at 280 m$\mu$, indicating that there is no protein contamination. Addition of bovine serum albumin (BSA), however, results in an absorption peak at 280 m$\mu$. The decrease in absorption with increasing proportions, relative to protein, of CaCl$_2$ is seen in FIG. 3, probably as a result of dilution of the protein. All samples were made up as 1% solutions and then diluted 10-fold before measurement. The percentages shown in FIGS. 1-3 refer to the concentrations before lyophilization.

Figure 4:
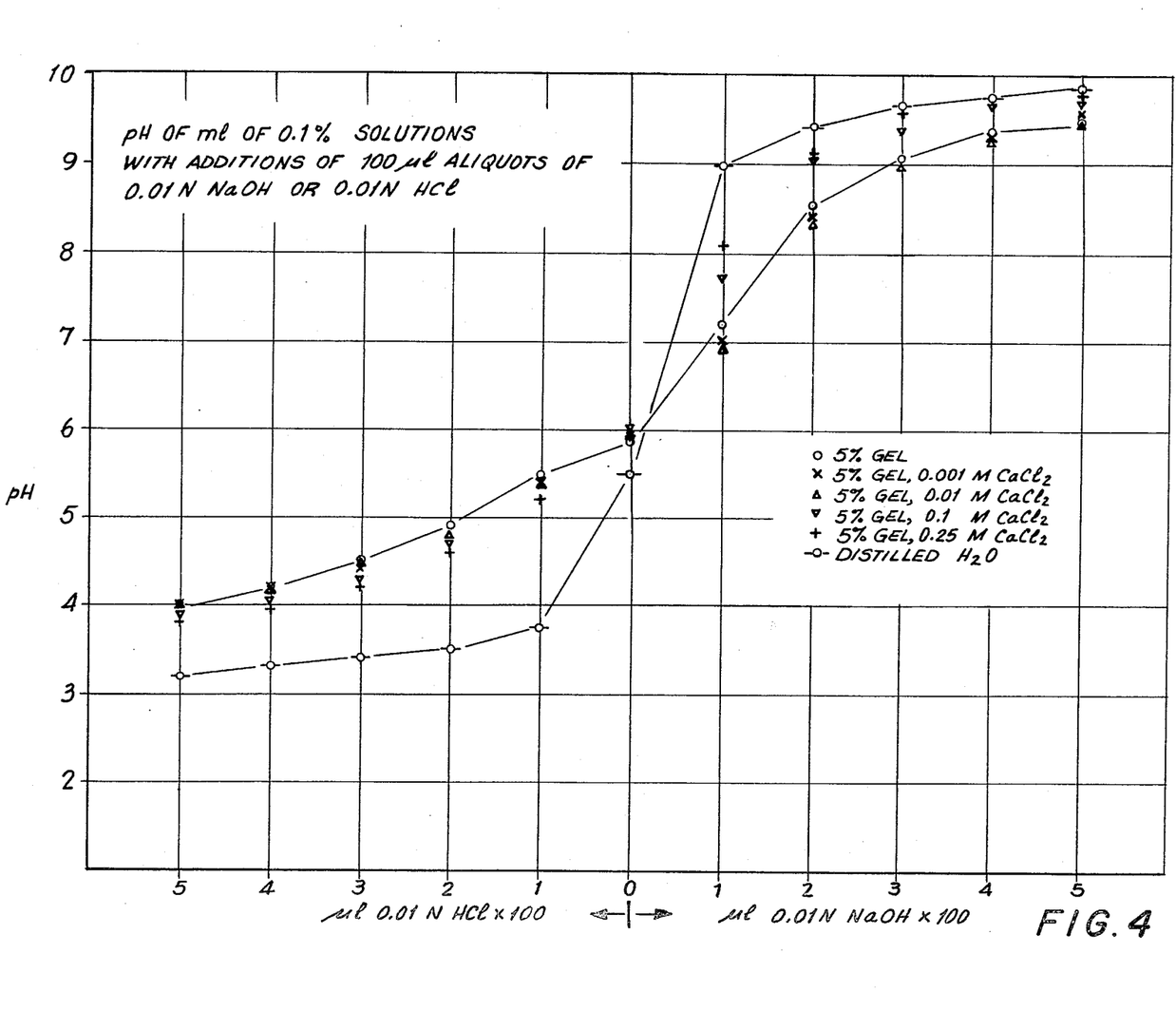
FIG. 4 is a chart showing the pH of solutions for the compounds of the invention.

FIG. 4 shows the pH of 10 ml of 0.1% Super Stat solutions with additions of 100$\mu$ liters of 0.01 N NaOH or 0.01 N HCl. The pH curve for distilled water, which has almost no buffering capacity, is also shown. With increasing proportion of CaCl$_2$ relative to protein, there is a decrease in buffering capacity, probably as a result of dilution of the protein. Also, additions of base result in a greater change in pH than do additions of acid. This difference is expected since: (1) The pH of the novel compound in distilled water (pH=5.5) is acidic, approximately 5.9, and (2) the net negative charge on the gel molecules would act to neutralize H+ more efficiently than OH.

Figure 5:
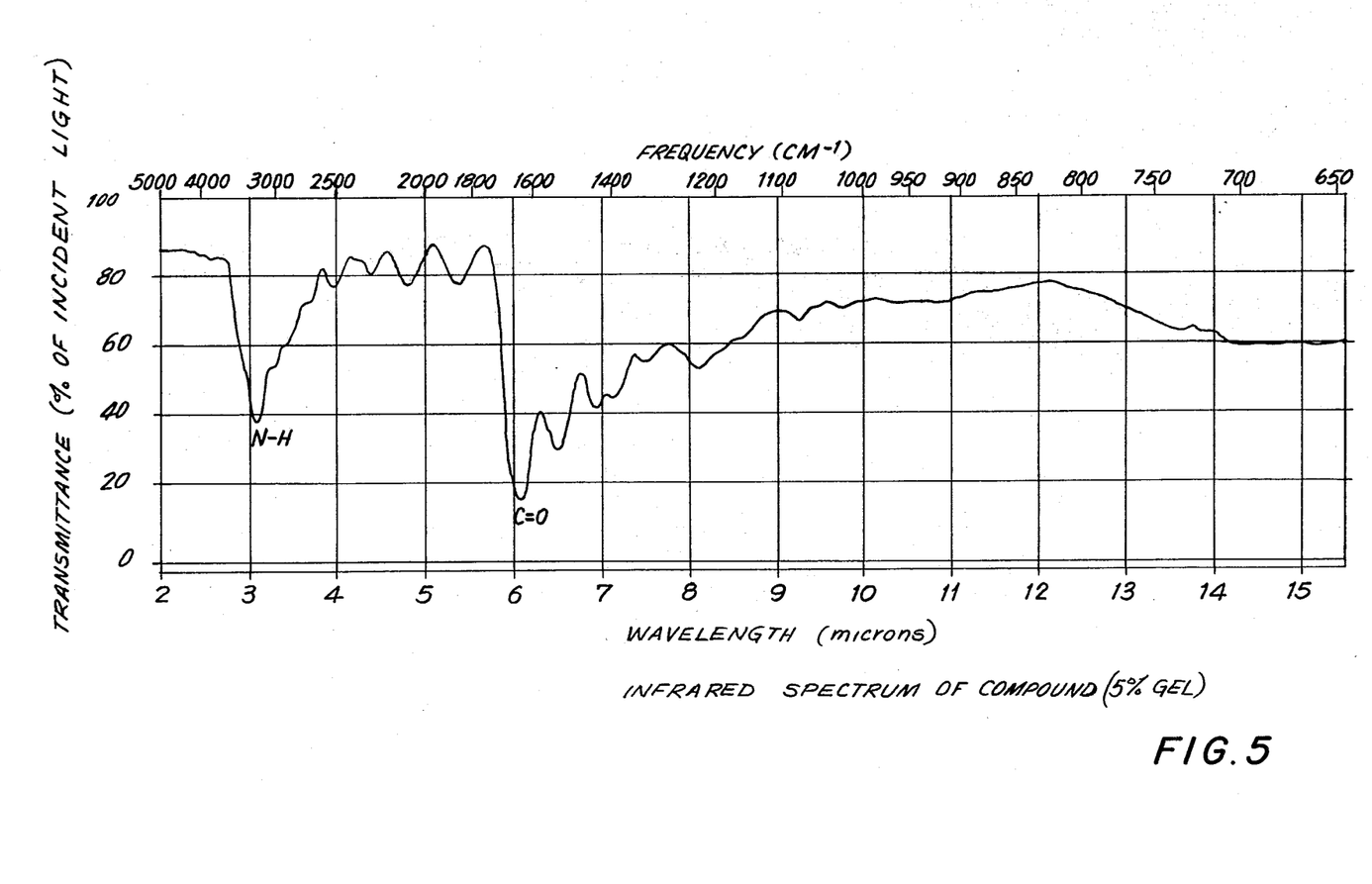
FIGS. 5 and 6 are charts of the infrared spectra of embodiments of the invention.
Figure 6:
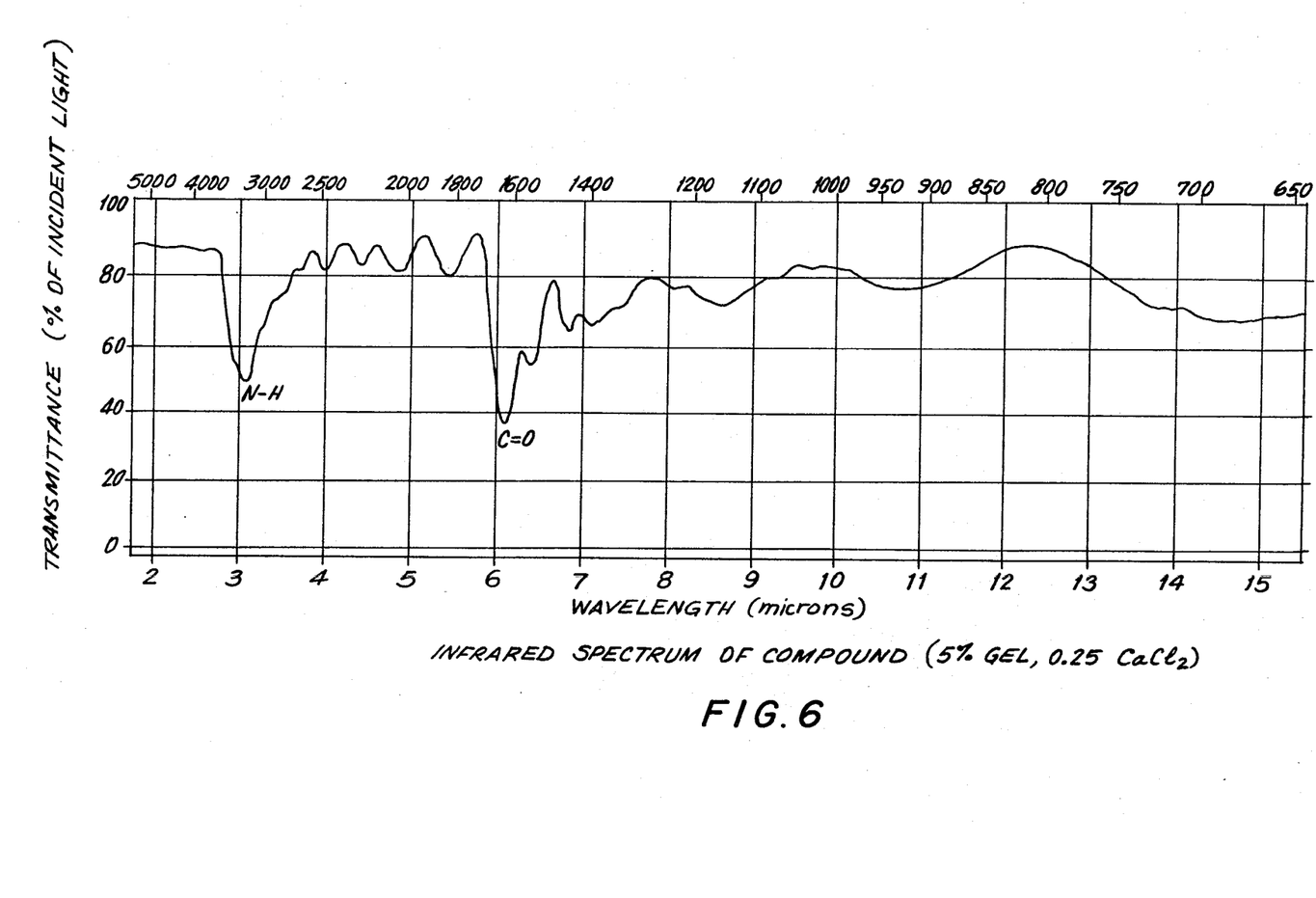

FIGS. 5 and 6 show the infrared spectra of the novel compounds. Absorption peaks for N-H and C=O are indicated. Increasing the proportion of CaCl$_2$ relative to protein results in a decrease in the two absorption peaks, as would be expected, but does not affect the shape of the peaks.

From the above, it will be seen that the invention provides the improved hemostatic agent as well as a method for producing the same. The invention also provides an improved method of controlling bleeding.

Although lyophilization techniques are known, the following steps may be used relative to the above disclosure:
1. Dispense 50 ml amounts into plastic 100 mm petri dishes.
2. Shelf-freeze in lyophilizer (e.g. Virtus model 100 SRC-7) at minus 30 to minus 50° C. for 3 to 5 hours or until eutectic point has been determined.
3. Set condenser for one to two hours; begin vacuum with no heat for 3 hours.
4. Set shelf heat to plus 30° C. and continue for 48 hours.

The following may be used for Sterilization:
1. Place in gas sterlization envelope and seal with indicator inside.
2. Gas sterilize with ethylene oxide through normal cycle.
3. Aerate thoroughly following exposure to ethylene oxide.

There will now be obvious to those skilled in the art many modifications and variations of the above embodiments. These modifications and variations will not depart from the scope of the invention if defined by the following claims.

What is claimed is:

1. A method comprising modifying one of the group consisting of collagen substance or a collagen-like substance by dissolving the substance in water and modifying the thusly dissolved substance to render the surface charge thereof effectively more positive than prior to modification, and freezing and drying the thusly modified substance and applying the thusly modified substance to control bleeding.

2. A method as claimed in claim 1 wherein the substance is modified by non-covalent modification.

3. A method as claimed in claim 2 wherein the substance is lyophilized.

4. A method comprising modifying one of the group consisting of collagen substance or a collagen-like substance to render the surface charge thereof effectively more positive, and applying the thusly modified substance to control bleeding, the substance being modified by covalent modification.

5. A method as claimed in claim 4 wherein the substance is lyophilized.

6. A hemostatic agent prepared as claimed in claim 1.

7. A hemostatic agent prepared as claimed in claim 3.

8. A hemostatic agent prepared as claimed in claim 5.

9. A method as claimed in claim 3 wherein the substance is gelatin which is treated with hydrochloric acid.

10. A method as claimed in claim 5 wherein the substance is gelatin which is treated with ethylenediamine.

11. A method as claimed in claim 5 wherein the substance is gelatin which is treated with NH$_4$Cl.

12. A method as claimed in claim 5 wherein the substance is gelatin which is treated with HCl.

13. A method of preparing a hemostatic agent comprising modifying one of the groups consisting of collagen substance or a collagen-like substance by dissolving the substance in water and modifying the thusly dissolved substance to render the surface charge thereof effectively more positive than prior to modification, and freezing and drying the thusly modified substance.

14. A method as claimed in claim 13 wherein the substance is modified by non-covalent modification.

15. A method as claimed in claim 14 wherein the substance is lyophilized.

16. A method of preparing a hemostatic agent comprising modifying one of the groups consisting of collagen substance or a collagen-like substance to render the surface charge thereof effectively more positive, the substance being modified by covalent modification.

17. A method as claimed in claim 16 wherein the substance is lyophilized.

18. A hemostatic agent prepared as claimed in claim 13.

19. A hemostatic agent prepared as claimed in claim 15.

20. A hemostatic agent prepared as claimed in claim 17.

21. A method as claimed in claim 15 wherein the substance is gelatin which is treated with hydrochloric acid.

22. A method as claimed in claim 17 wherein the substance is gelatin which is treated with ethylenediamine.

23. A method as claimed in claim 17 wherein the substance is gelatin which is treated with $NH_4Cl$.

24. A method as claimed in claim 17 wherein the substance is gelatin which is treated with HCl.

25. A method as claimed in claim 15 wherein the substance is gelatin which is treated with calcium.

26. A method as claimed in claim 25 wherein the calcium is used in the form of calcium chloride.

* * * * *